United States Patent [19]

Ebata et al.

[11] Patent Number: 5,175,366
[45] Date of Patent: Dec. 29, 1992

[54] PROCESS FOR PRODUCING A DENATURATED MANGANESE DIOXIDE CATALYST FOR THE HYDRATION REACTION OF CYANOHYDRINS

[75] Inventors: Shuji Ebata; Hiroyuki Hirayama; Hirofumi Higuchi; Koichi Kida, all of Niigata, Japan

[73] Assignee: Mitsubishi Gas Chemical Company, Inc., Tokyo, Japan

[21] Appl. No.: 744,954

[22] Filed: Aug. 14, 1991

Related U.S. Application Data

[62] Division of Ser. No. 542,835, Jun. 25, 1990, Pat. No. 5,061,675.

[30] Foreign Application Priority Data

Aug. 8, 1989 [JP] Japan .................................. 1-203790

[51] Int. Cl.⁵ .......................................... C07C 231/06
[52] U.S. Cl. .................................. 564/126; 502/324
[58] Field of Search ........................................ 564/126

[56] References Cited

U.S. PATENT DOCUMENTS

| | | | |
|---|---|---|---|
| 1,602,404 | 10/1926 | Frazer | 502/324 |
| 3,366,639 | 1/1968 | Haefele et al. | 260/245 |
| 3,699,164 | 10/1972 | Fine et al. | 260/561 N |
| 4,018,829 | 4/1997 | Gruber et al. | 260/561 B |

FOREIGN PATENT DOCUMENTS

| | | |
|---|---|---|
| 0379111 | 7/1990 | European Pat. Off. . |
| 1157590 | 11/1963 | Fed. Rep. of Germany ...... 423/625 |
| 1593320 | 10/1971 | Fed. Rep. of Germany . |
| 209429 | 5/1984 | German Democratic Rep. . |
| 51-71299 | 12/1974 | Japan . |
| 63-57534 | 3/1988 | Japan . |
| 63-57535 | 3/1988 | Japan . |

OTHER PUBLICATIONS

Database WPI, No. 77-67710Y, Derwent Publications Ltd. London, GB; for JP-A-52 095 597.
Database WPI, No. 76-59058X, Derwent Publications Ltd. London, GB; for JP-A-51 071 299 Abstract.

*Primary Examiner*—Carolyn Elmore
*Assistant Examiner*—Shailendra Kumar
*Attorney, Agent, or Firm*—Frishauf, Holtz, Goodman & Woodward

[57] ABSTRACT

A process for preparing an amide by hydrating a cyanohydrin with a denatured manganese dioxide catalyst. The catalyst is prepared by reacting an aqueous permanganate solution and an aqueous manganese (II) compound solution in an acidic aqueous solution at a temperature of 70° C. to 150° C.

9 Claims, No Drawings

PROCESS FOR PRODUCING A DENATURATED MANGANESE DIOXIDE CATALYST FOR THE HYDRATION REACTION OF CYANOHYDRINS

This is a division of application Ser. No. 07/542,835 filed Jun. 25, 1990 now U.S. Pat. No. 5,061,675 issued Oct. 29, 1991.

BACKGROUND OF THE INVENTION

1. Field of the Invention

The present invention relates to a process for producing a denaturated manganese dioxide catalyst for the hydration reaction of cyanohydrins. More particularly, the present invention relates to a process for producing efficiently manganese dioxide having a high catalytic activity for the hydration reaction of cyanohydrin in an aqueous phase.

2. Description of the Related Arts

The reaction for synthesizing an amide from a corresponding nitrile can be applied, for example, to the production of acrylamide from acrylonitrile or the production of methyl methacrylate from acetone cyanohydrin by way of α-hydroxyisobutyric acid amide. The development of an excellent catalyst for the synthetic reaction of amides starting from the corresponding nitriles is of great significance from the industrial standpoint.

It has already been well known that manganese dioxide is used as a catalyst for the synthesis of an amide by the hydration reaction of a nitrile, and a variety of methods for preparing the catalyst have been proposed. For example, it is disclosed in West Germany Patent No. 1593320 that manganese dioxide is prepared by reacting manganese sulfate and potassium permanganate in an equivalent amount at a temperature of 80° C. in the presence of a little excessive amount of sodium hydroxide.

It is also disclosed in U.S. Pat. No. 4,018,829 that δ-type manganese dioxide is suitable for a catalyst in the hydration reaction of acetone cyanohydrin. The δ-type manganese dioxide, as described in Z. Anorg. Allg. Chem., 309 (1961), pages 10 to 14, is produced by the reduction of a manganese (VII) compound in the neutral to alkaline pH at a temperature of 20° to 100° C.

Moreover, as the production methods of amide compounds from nitriles, there are disclosed a method for utilizing a catalyst prepared by incorporating zinc into manganese dioxide which has been prepared from potassium permanganate and manganese sulfate in Japanese Patent Application Laid-Open No. 57534/1988 and a method for utilizing, as a catalyst, manganese dioxide which has been obtained by the reduction of an alkaline aqueous solution of potassium permanganese with hydrochloric acid in Japanese Patent Application Laid-Open No. 57535/1988.

Manganese dioxide prepared by the conventional methods as described above has problems that (1) a satisfactory yield of an amide as a target cannot be obtained when the manganese dioxide is directly used as a catalyst of the hydration reaction of cyanohydrins, (2) the activity of the manganese dioxide is insufficient and thus the amount of the catalyst to be used is increased, and (3) the catalytic activity is rapidly lowered during its repeated use. Accordingly, the aforementioned manganese dioxide catalyst has not yet been used in practice.

The present inventors have conducted research earnestly for the purpose of producing a manganese dioxide catalyst for the hydration reaction of cyanohydrins free from the aforementioned problems. Particularly, earnest research has been conducted on the requirements for preparing a manganese dioxide catalyst for the hydration reaction of cyanohydrins starting from a permanganate salt and a manganese (II) compound. As a result, it has been found that a denaturated manganese dioxide prepared with a specified starting materials under a prescribed temperature condition exhibits an extremely high catalytic activity and a long lifetime as a catalyst. The present invention has been accomplished on the basis of such findings.

SUMMARY OF THE INVENTION

The object of the present invention is to provide a high active manganese dioxide catalyst for the hydration reaction of cyanohydrins.

Another object of the present invention is to provide a manganese dioxide which has a high activity and a long lifetime as a catalyst for the hydration reaction of cyanohydrins.

A further object of the present invention is to provide efficiently an amide by the hydration reaction of corresponding cyanohydrins.

That is to say, the present invention provides a process for producing a denaturated manganese dioxide catalyst for the hydration reaction of cyanohydrins, which process comprises reacting a permanganate salt and a manganese (II) compound in an acidic aqueous solution at a temperature of 60° C. to 150° C.

DESCRIPTION OF PREFERRED EMBODIMENTS

The present invention will be described in detail below.

Manganese dioxide is used in the hydration reaction of cyanohydrins as already described above, in which manganese dioxide has a general composition of $MnO_{1.7}$ to $MnO_2$ and crystal structures such as α, β, γ, δ and ε. Furthermore, in manganese dioxide, a transition between respective phases or a change in the crystallinity occurs so that its structure is very complicated and varied. While manganese dioxide is present in nature, it is usually prepared by the oxidation of manganese (II) compounds or the reduction of permanganate (VII) salts on its use as a catalyst.

The process according to the present invention belongs to the process for preparing a denaturated manganese dioxide from an excessive amount of a permanganate (VII) salt and a manganese (II) compound in an acidic aqueous solution.

The aqueous solutions of permanganate salts generally have different reactivities depending on the properties of the solutions, particularly pH.

In the strong alkaline condition, the permanganate releases oxygen to produce manganic acid (VI) with the reaction of the equation (1):

$$4MnO_4^- + 4OH^- \rightarrow 4MnO_4^{2-} + 2H_2O + O_2 \qquad (1).$$

In the neutral or acidic condition, the permanganate gradually decomposes and releases oxygen to form manganese dioxide with the reaction of the equation (2):

$$4MnO_4^- + 4H^+ \rightarrow 4MnO_2 + 2H_2O + 3O_2 \qquad (2).$$

In this connection, the redox reaction of an aqueous permanganate solution proceeds according to the equation (3) under an acidic condition and according to the equation (4) under the neutral or alkaline condition:

$$MnO_4^- \rightarrow Mn^{2+} \quad (3); \quad MnO_4^- \rightarrow MnO_2 \quad (4)$$

In the acidic condition, manganese dioxide is produced by the reaction of the equation (5) (Guyard reaction):

$$2MnO_4^- + 3Mn^{2+} + 2H_2O \rightarrow 5MnO_2 + 4H^+ \quad (5)$$

Accordingly, in an acidic aqueous solution, manganese dioxide can be prepared by the reactions represented by the equations (2), (3) and (5) with an excessive amount of permanganate salt and a manganese (II) compound.

The term "permanganate salt" used herein means one or more compounds selected from lithium permanganate, sodium permanganate and potassium permanganate. The term "manganese (II) compound" means one or more compounds selected from manganese sulfate, manganese nitrate and manganese chloride.

The reaction is conducted at a temperature in the range of 60° to 150° C., preferably 70° to 130° C. in the present invention. If the reaction is carried out at a temperature lower than that specified above, the reaction rate becomes low. If the reaction is carried out at a temperature higher than that specified above, the catalytic activity of the resulting denaturated manganese dioxide is decreased.

In the reaction of the present invention, the molar ratio of the permanganate salt to the manganese (II) compound is not critical, and it is usually in the range of 1/1 to 5/1, preferably in the range of 1.2/1 to 3/1. The permanganate salt and the manganese (II) compound are used in the form of aqueous solutions and are respectively used in high concentrations within their ranges of solubility or within the ranges that will not affect stirring operation. For instance, if the permanganate salt is an aqueous solution of potassium permanganate, the aqueous solution is preferably in the concentration of 1 to 3 moles/liter. If the manganese (II) compound is an aqueous solution of manganese sulfate, the aqueous solution is preferably in the concentration of 2 to 4 moles/liter.

As the acid in the acidic aqueous solution in the present invention, there is used a mineral acid such as sulfuric acid, nitric acid, hydrochloric acid or the like, preferably sulfuric acid. The amount of the acid used is not specifically limited. It may be appropriately set depending on the situations and its molar ratio of the acid to the permanganate salt is in the range of 0.1/1 to 2/1, preferably in the range of 0.2/1 to 1/1.

In the present invention, the denaturated manganese dioxide prepared as above is isolated and formed into a tablet or molded by extrusion to give a catalyst for a fixed bed, or it can be used directly in the form of powder as a slurry catalyst, which is applied to a batchwise or continuous reactor for the hydration reaction of cyanohydrins.

Cyanohydrins to be used in the present invention include aliphatic cyanohydrins having 2 to 8 carbon atoms. Specific examples of the aliphatic cyanohydrins are glycolonitrile, lactonitrile, acetone cyanohydrin and methyl ethyl ketone cyanohydrin.

The denaturated manganese dioxide prepared according to the process of the present invention can develop a high activity with a long lifetime as a catalyst for the hydration reaction of cyanohydrins. It is also possible to produce efficiently an amide by the hydration reaction of the corresponding cyanohydrin with the aforementioned catalyst.

Accordingly, the process of the present invention is of great industrial significance.

The present invention is described below in more detail with reference to Examples. The present invention is not limited thereto.

EXAMPLE 1

(1) Preparation of catalyst: To a solution of 66.4 g (0.42 mole) of potassium permanganate dissolved in 250 ml of water, a mixture of 141 g (0.28 mole) of a 30% by weight aqueous manganese sulfate solution and 23.9 g of concentrated sulfuric acid were added rapidly at a temperature of 70° C., and the mixture was allowed to react.

The resulting precipitate was stirred at 90° C. for 3 hours, filtered and washed three times with 500 ml of water followed by drying overnight at 110° C. to give 65.9 g of a black mass of manganese dioxide as catalyst.

(2) Hydration reaction: The manganese dioxide obtained in the aforementioned paragraph (1) was ground and passed through a sieve to give particles having size of 10 to 20 mesh, which was packed in a glass tubular reactor equipped with a jacket and having an internal diameter of 10 mm. Warm water at 60° C. was flown through the jacket, and a raw material solution consisting of a mixture of 20 g of acetone cyanohydrin, 60 g of water and 20 g of acetone was passed through the reactor at a flow rate of 5 g/hr.

The reaction mixture after 5 hours had a composition of 23% by weight of α-hydroxyisobutyric acid amide, 0.1% by weight of acetone cyanohydrin, 21.0% by weight of acetone and 0.4% by weight of formaldehyde upon the determination by high performance liquid chromatography. Such yields correspond to the α-hydroxyisobutyric acid amide of 95% (based on the acetone cyanohydrin as the raw material).

The reaction was further continued for 1 week. As the result of the composition analysis of the reaction mixture for the second time, the yield of α-hydroxyisobutyric acid amide was 95%.

COMPARATIVE EXAMPLE 1

(1) Preparation of catalyst: To a solution of 19.2 g (0.12 mole) of potassium permanganate dissolved in 120 ml of water, a solution of 22.2 g (0.10 to 0.086 mole) of manganese sulfate tetrahydrate to hexahydrate and 6.7 g of potassium hydroxide dissolved in 30 ml of water was added rapidly at a temperature of 70° C., and the mixture was allowed to react.

The resulting precipitate was stirred at 70° C. for 3 hours, filtered and washed three times with 200 ml of water followed by drying overnight at 110° C. to give 23.8 g of a brown mass of manganese dioxide as catalyst.

(2) Hydration reaction: A 3.5 g portion of the catalyst prepared in the aforementioned paragraph (1) was used to conduct the hydration reaction in the same manner as in Example 1.

As the result, the yields of α-hydroxyisobutyric acid amide after 5 hours and 1 week were 74% and 41%, respectively.

COMPARATIVE EXAMPLE 2

(1) Preparation of catalyst: To a solution of 19 g (0.12 mole) of potassium permanganate dissolved in 200 ml of water, a solution of 22.2 g (0.1 to 0.086 mole) of manganese sulfate tetrahydrate to hexahydrate and 10.2 g of concentrated sulfuric acid dissolved in 60 ml of water was added at a temperature of 50° C. over a period of 10 minutes, and the mixture was allowed to react.

The resulting precipitate was stirred at 50° C. for 10 hours, filtered and washed three times with 200 ml of water followed by drying overnight at 110° C. to give 23.1 g of a brown mass of manganese dioxide as catalyst.

(2) Hydration reaction: A 3.4 g portion of the catalyst prepared in the aforementioned paragraph (1) was used to conduct the hydration reaction in the same manner as in Example 1.

As the result, the yields of α-hydroxyisobutyric acid amide after 5 hours and 1 week were 58% and 11%, respectively.

COMPARATIVE EXAMPLE 3

(1) Preparation of catalyst: To a solution of 12.6 g (0.08 mole) of potassium permanganate dissolved in 120 ml of water, a solution of 22.2 g (0.1 to 0.086 mole) of manganese sulfate tetrahydrate to hexahydrate and 2.5 g of concentrated sulfuric acid dissolved in 30 ml of water was added rapidly at a temperature of 70° C., and the mixture was allowed to react.

The resulting precipitate was stirred at 70° C. for 3 hours, filtered and washed three times with 200 ml of water followed by drying overnight at 110° C. to give 18.4 g of a black mass of manganese dioxide as catalyst.

(2) Hydration reaction: A 3.5 g portion of the catalyst prepared in the aforementioned paragraph (1) was used to conduct the hydration reaction in the same manner as in Example 1.

As the result, the yields of α-hydroxyisobutyric acid amide after 5 hours and 1 week were 94% and 62%, respectively.

EXAMPLE 2

(1) Preparation of catalyst: A 12.8 g amount of potassium permanganate was dissolved in 140 ml of water, and 2.5 g of concentrated sulfuric acid was added thereto.

To the resulting solution was added 22.2 g of manganese sulfate tetrahydrate to hexahydrate dissolved in 30 ml of water at a temperature of 70° C., and the mixture was allowed to react. Agitation was continued for 3 hours at 80° C. The mixture was cooled to room temperature, filtered and washed three times with 200 ml of water followed by drying overnight at 110° C. to give 22.5 g of a black mass of manganese dioxide as catalyst.

(2) Hydration reaction: A 3.5 g portion of the catalyst prepared in the aforementioned paragraph (1) was used to conduct the hydration reaction in the same manner as in Example 1 except that methyl ethyl ketone cyanohydrin was used in place of acetone cyanohydrin and methyl ethyl ketone was used in place of acetone.

As the result, the yields of 2-hydroxy-2-methylbutyric acid amide after 5 hours and 1 week were 85% and 88% respectively.

EXAMPLE 3

The same procedure was carried out as in Example 1 with the exception that lactonitrile was used in place of acetone cyanohydrin, and that raw material consisting of 20% by weight of lactonitrile and 80% by weight of water was passed through the reactor at a flow rate of 5.5 g/hr at a temperature of 50° C.

As the result, the yields of lactic acid amide after 5 hours and 1 week were 97% and 95%, respectively.

What is claimed is:

1. A process for preparing an amide comprising subjecting a cyanohydrin to hydration reaction with the denaturated manganese dioxide catalyst prepared by the process comprising reacting an aqueous permanganate solution and an aqueous manganese (II) compound solution in an acidic aqueous solution at a temperature of 70°C. to 150° C.

2. A process according to claim 1, wherein the cyanohydrin is an aliphatic cyanohydrin having 2 to 8 carbon atoms.

3. A process according to claim 1, wherein the cyanohydrin is at least one compound selected from the group consisting of glycolonitrile, lactonitrile, acetone cyanohydrin and methyl ethyl ketone cyanohydrin.

4. The process according to claim 1, wherein said amide is α-hydroxyisobutyric acid amide which is prepared by hydration of acetone cyanohydrin in the presence of a large amount of acetone and water.

5. The process according to claim 1, wherein said amide is 2-hydroxy-2-methylbutyric acid amide which is prepared by hydration of methyl ethyl ketone cyanohydrin in the presence of methyl ethyl ketone and water.

6. The process according to claim 1, wherein said amide is lactic acid amide which is prepared by hydration of lactonitrile which was hydrated with water.

7. The process according to claim 4, wherein an aqueous solution of potassium permanganate is reacted with an aqueous solution of manganese sulfate in the presence of sulfuric acid.

8. The process according to claim 5, wherein an aqueous solution of potassium permanganate is reacted with an aqueous solution of manganese sulfate in the presence of sulfuric acid.

9. The process according to claim 6, wherein an aqueous solution of potassium permanganate is reacted with an aqueous solution of manganese sulfate in the presence of sulfuric acid.

* * * * *